US 6,554,861 B2

(12) United States Patent
Knox et al.

(10) Patent No.: US 6,554,861 B2
(45) Date of Patent: *Apr. 29, 2003

(54) OTOLOGIC PROSTHESIS

(75) Inventors: Glenn W. Knox, Jacksonville, FL (US); Harlan Reitan, Collierville, TN (US)

(73) Assignee: Gyrus ENT L.L.C., Bartlett, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/798,400

(22) Filed: Mar. 2, 2001

(65) Prior Publication Data

US 2001/0037151 A1 Nov. 1, 2001

Related U.S. Application Data

(63) Continuation-in-part of application No. 09/233,394, filed on Jan. 19, 1999, now Pat. No. 6,197,060.

(51) Int. Cl.⁷ .................................................. A61F 2/18
(52) U.S. Cl. .......................................... 623/10; 600/25
(58) Field of Search ................... 623/10, 11.11; 600/25

(56) References Cited

U.S. PATENT DOCUMENTS

| 3,191,188 A | 6/1965 | Mercandino et al. ............. 3/1 |
| 3,196,462 A | 7/1965 | Robinson ......................... 3/1 |
| 3,711,869 A | 1/1973 | Shea, Jr. ......................... 3/1 |
| 3,838,468 A | 10/1974 | Armstrong ...................... 3/1 |
| 3,931,648 A | 1/1976 | Shea, Jr. ....................... 3/1.9 |
| 4,292,693 A | 10/1981 | Shea et al. ..................... 3/1.9 |
| 4,514,177 A | 4/1985 | Lenkoff ....................... 434/328 |
| 4,740,209 A | 4/1988 | Gersdorff ...................... 623/10 |
| 4,957,507 A | 9/1990 | Lenkauskas .................. 623/10 |
| 5,171,240 A | 12/1992 | Hanwong ....................... 606/1 |
| 5,302,117 A | 4/1994 | Kraut et al. ................... 433/21 |
| 5,370,689 A | 12/1994 | Causse ......................... 623/10 |
| 5,433,749 A | 7/1995 | Clifford et al. ............... 623/10 |
| 6,197,060 B1 * | 3/2001 | Knox ........................... 623/10 |

FOREIGN PATENT DOCUMENTS

| EP | 0 379 740 A1 | 8/1990 | ............. A61F/2/18 |
| EP | 0 909 554 A1 | 4/1999 | ............. A61F/2/18 |
| WO | WO 98/22042 | 5/1998 | ............. A61F/2/06 |
| WO | WO 98/24371 | 6/1998 | ........... A61B/17/00 |

OTHER PUBLICATIONS

Database WPI, Section PQ, Week 9207, Derwent Publications Limited, London, GB; An 92–054843 XP002136222 & SU 1 634 272 A (Tomsk Univ. Sube. Phys.), Mar. 15, 1991 Abstract.

Fujihiko Kasano et al., "Utilization of Nickel–Titanium Shape Memory Alloy for Stapes Prosthesis", Auris Nasus Larynx, vol. 24, pp. 127–142 (1997).

\* cited by examiner

Primary Examiner—David J. Isabella
(74) Attorney, Agent, or Firm—Oliff & Berridge, PLC

(57) ABSTRACT

Otologic prosthesis of shape memory metal alloy self-secure about an otologic structure when heat is applied to a preformed bight by means of a laser.

30 Claims, 7 Drawing Sheets

OTOLOGIC PROSTHESIS

This application is a continuation-in-part of a application, Ser. No. 09/233,394, filed Jan. 19, 1999 now U.S. Pat. No. 6,197,060.

TECHNICAL FIELD

The present invention relates generally to otologic prostheses; and more particularly to a novel and improved otologic prosthesis for relieving impaired conductive hearing of the middle ear.

BACKGROUND

Otosclerosis is a common cause of progressive conductive hearing loss in which softening and hardening of minute areas of the ossicles (malleus, incus and stapes) in the middle ear produce abnormal bone growth and impede conduction of sound vibration from the eardrum to the inner ear. In about ten percent of patients with otosclerosis, the bone growth spreads to the stapes bone in particular, the final link in the middle ear chain. The stapes is a small stirrups-shaped bone with its base resting in a small groove, commonly called the oval window, in intimate contact with the inner ear fluids. When the amount of otosclerosis at this location is significant, as determined by careful hearing tests, a stapedectomy (or stapedotomy) is the treatment of choice.

A stapedectomy is a microsurgical technique in which a portion of the stapes or stapes arch is replaced by a prosthesis. When the procedure was first introduced in the 1950s, many surgeons became skilled in the technique and while many more surgeons, on an average, now perform it there are relatively few performed per surgeon. Hence, proficiency is harder to maintain for the occasional stapes surgeon.

A stapedectomy is usually performed through an incision in the ear canal under local or general anesthesia. A flap consisting of canal skin and the tympanic membrane (eardrum) is elevated and the posterior superior bony external auditory canal is drilled away to expose the stapes, incus, and chorda tympani (facial nerve). The ossicles are palpated to confirm fixation of the stapes and mobility of the malleus and incus.

With care taken to preserve the chorda tympani, the joint between the incus and the stapes is separated with a knife, and a laser or other microsurgical instrument severs the stapes tendon and one crus (leg) of the stapes. The arch of the stapes bone may then be removed by fracturing off the other crus allowing the footplate to remain in the oval window. A laser is used to form a minuscule hole in the footplate for posting the stapedial prosthesis. In some cases, the footplate is also removed by a so-called "large hole" technique and a vein grafted to the internal wall of the tympanum to cover the opening and to support the prosthesis.

After a hole is made in the footplate (or tissue is placed over the opening to the inner ear made after removing the footplate) one end of a biocompatible plastic or metal piston-like stapedial prosthesis of proper length is posted in the hole and the other end attached to the incus. A piece of fat or other tissue is taken, such as from a small incision behind the ear lobe, to seal any hole in the window, and the eardrum is folded back into its normal position with a small gelatin sponge to hold it in position.

A critical part of the procedure is attaching the prosthesis around the lenticular process of the incus due to its minuteness and delicate nature, typically about 3.5 mm to 6 mm long and 0.6 mm to 0.8 mm diameter. For instance, in U.S. Pat. No. 5,370,689 to Causse one end of the prosthesis fabricated of PTFE is posted in a hole drilled in the exposed footplate and a split eyelet at the other end must be crimped around the incus. In U.S. Pat. No. 3,714,869 to Shay Jr. one end of the prosthesis is placed on a vein graft invaginated into the oval window, and a split eyelet at the other end must be forced open by elastic deformation to fit onto the incus. Elastic recovery capacity of the eyelet causes it to restore to its original form in about 20 minutes and grip the incus firmly. U.S. Pat. No. 3,838,468 to Armstrong discloses a stapedial prosthesis for use in cases where the footplate is also removed. A piston is fixed at one end to a vein graft for covering the oval window. A wire of stainless steel, platinum, gold, or like biocompatible material shaped like a shepherd's crook extending from the other end, is crimped about the lenticular process of the incus. U.S. Pat. No. 5,433,749 to Clifford et al. discloses a stapedial prosthesis of metal or plastic in which one end of a piston extends into the fluid in the inner ear and the other end is secured to the incus by a separate heat-shrinkable sleeve when heat is applied as by a laser.

It is readily apparent that great care and skill are required to secure these and similar prostheses to the lenticular process of the incus. The minute size of the prostheses also makes them extremely difficult to manipulate into proper position for tightening around the incus, even with state-of-the-art microsurgical instrumentation. Once in place, if the prosthesis is not tightened sufficiently about the incus, fluctuating hearing loss, dizziness, or extrusion of the prosthesis may occur. If it is too tight, necrosis of the incus may occur. In either case, the tightening procedure in itself may cause trauma to the delicate middle ear structures, including fracture or subluxation (dislocation) of the incus.

Other otologic prostheses may be implanted by similar procedures directly between the malleus and the footplate of the stapes or the oval window of the inner ear.

SUMMARY

This invention features an otologic prosthesis which can be installed easily with confidence by the occasional ossicle replacement surgeon and with few complications and good hearing results.

The invention also features an otologic prosthesis, which can be readily connected to an ossicle with little trauma to the delicate middle ear structures.

The invention further features a stapedial prosthesis which is relatively simple in construction, utilizes state-of-the-art materials, and which can be easily manipulated in the middle ear.

In one general aspect of the invention, an otologic prosthesis of biocompatible shape memory alloy for conducting sound vibration from the eardrum, through the inner ear, to the oval window of the inner ear. One embodiment of the invention is a stapedial prosthesis including a shaft of nickel-titanium wire having means on one end portion for posting in a hole formed in the footplate of the stapes. The other end portion of the shaft, in a thermoelastic martensitic phase, is reversely turned to form a bight, as manufactured, to fit snugly around the lenticular process of the incus when installed. The bight is plastically deformable at ambient temperatures to fit loosely against the incus. When the wire temperature is elevated to a higher temperature, as by application of a laser beam, the bight returns to its memorized shape for positively embracing the incus. Preferably, a heat sink flange is mounted on the shaft for conducting heat to the bight when the laser energy is applied. Other embodiments of prostheses are disclosed.

In one aspect, the invention features an apparatus having an elongated member with a first end and a second end. The first end defines a first bight lying substantially in a first plane. The first end is deformable to open the first bight to receive a first otologic structure and configured to substantially close the first bight in response to an applied signal thereby to capture the first otologic structure. The second end defines a second bight lying substantially in a second plane transverse to the first plane. The second end is deformable to open said second bight to receive a second otologic structure and configured to substantially close the second bight in response to an applied signal thereby to capture the second otologic structure with the second bight.

In another aspect, the invention features an apparatus having an elongated member with a first end and a second end. The first end defines a first bight lying substantially in a plane. The first end is deformable in response to an applied signal to open the first bight to receive an otologic structure. The first end is configured to substantially close the first bight in response to an applied signal thereby to capture the first otologic structure. The second end defines a second bight lying substantially in the plane. The second end is deformable in response to an applied signal to open the second bight to receive a second otologic structure. The second end is configured to substantially close the second bight in response to an applied signal thereby to capture the second otologic structure.

In another aspect, the invention features an elongated member having a first end and a second end. The first end defines a first bight lying substantially in a first plane. The first end is deformable in response to an applied signal to open the first bight to receive a first otologic structure. The first end is configured to substantially close the first bight in response to an applied signal thereby to capture the first otologic structure. The second end of the member includes an enlarged surface area sized and oriented to lie substantially flat against and be secured to a second otologic structure. The second end receives sound vibrations from the second otologic structure.

In another aspect, the invention features a method including providing an otologic implant having an end defining a bight. The end is deformed to open the bight to receive an otologic structure. Applying a signal to the implant substantially closes the bight and captures the otologic structure.

Preferred embodiments may include one or more of the following features. The first otologic structure is a malleus or an incus and the second otologic structure is a portion of the stapes arch or a capitulum. The member is formed of biocompatible, shape-memory alloy.

The enlarged surface is substantially planar and is oriented at an angle to the member within a range of about 30 degrees to about 90 degrees. The first otologic structure is an incus, a portion of the stapes arch, or a capitulum and the second otologic structure is an eardrum. The apparatus includes an adhesive.

The provided implant includes a first end defining a first bight and a second end defining a second bight. The first end is deformed to open the first bight and the second end is deformed to open the second bight. A signal applied to the implant captures the first otologic structure and the second otologic structure. The signal is heat. The otologic structure is a malleus.

Embodiments of the invention may have one or more of the following advantages. The shape-memory alloy permits at least one end of the implant to be secured to an otologic structure without having to insert a securement tool in the middle ear. The implant may be deformed to a shape that readily permits positioning of the implant to capture an otologic structure. A surgeon controls the initiation of returning the prosthesis to its predetermined shape. The prosthesis combines heat-activated capture of an otologic structure with the structural properties of a metal alloy.

The details of one or more embodiments of the invention are set forth in the accompanying drawings and the description below. Other features, objects, and advantages of the invention will be apparent from the description and drawings, and from the claims.

DESCRIPTION OF DRAWINGS

The foregoing and other objects, features and advantages of the present invention should become apparent from the following drawings, in which.

DETAILED DESCRIPTION

Figure 1:
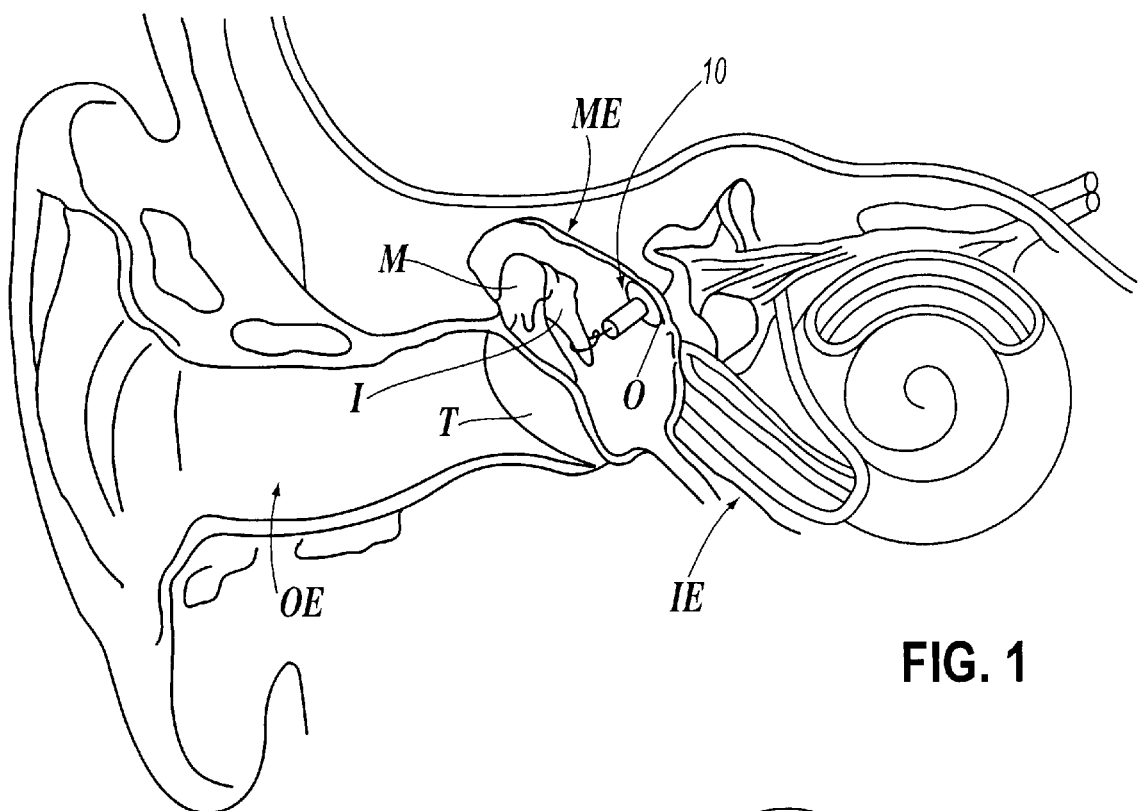
FIG. 1 is an enlarged, fragmentary, partially broken-away, perspective view of a human ear having one embodiment of an otologic prosthesis according to the present invention.

Referring now to the drawings, FIG. 1 illustrates a human ear having an outer ear structure OE, a middle ear structure ME, and an inner ear structure IE. The middle ear ME is separated from the outer ear OE by the tympanic membrane T. The malleus M is connected to the tympanic membrane T and the incus I is connected to the malleus M. One example of an otologic prosthesis 10 connects the incus I to the oval window O adjacent the inner ear IE.

The otologic prosthesis 10 illustrated in FIG. 1 is used in a so-called stapedectomy. When installed, the otologic prosthesis 10 provides a sound-conductive connection between a first otologic structure, such as the incus process I, and a second otologic structure, such as the oval window O. When installed as illustrated, vibrations from the incus process I are transmitted to the oval window O in the same manner as with a conventional prosthesis.

As discussed heretofore, a significant problem that exists with a conventional otologic prosthesis of the type described resides in the connection of the outer end of the prosthesis to the incus process. Presently, it is necessary to crimp the outer end of a wire-form prosthesis about the incus process and, because it requires great care, it is a difficult and time-consuming portion of the overall stapedectomy procedure.

According to the present invention, the problems associated with prior art otologic prostheses are overcome by the otologic prosthesis 10, which comprises an elongate shaft 11 of nickel-titanium metal wire alloy having biocompatible shape-memory properties, such as Nitinol. The shaft 11 has an upper, or outer, end portion 12 that is reversely turned on itself to form an open-ended bight 13 (see, e.g., FIG. 2). As manufactured, the prosthesis 10 has an overall length of about 4 mm, and the reversely turned bight has a radius of approximately 0.05 mm. The diameter of the wire shaft is approximately 0.005 mm. The bight 13 is adapted to engage the incus process I as illustrated in FIG. 3D in the manner to be discussed.

Figure 2:
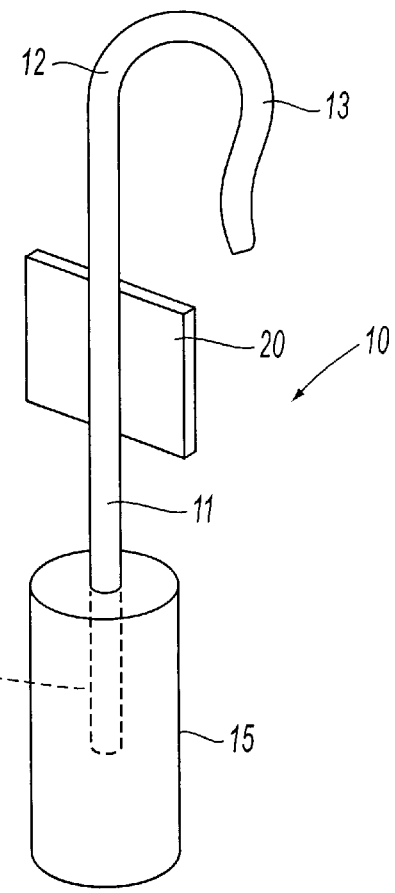
FIG. 2 is an enlarged perspective view of the otolithic prosthesis illustrated in FIG. 1.
Figure 3A:
FIGS. 3A–3D are perspective views of the prosthesis embodiment of FIG. 1, but showing it in various phases of installation on an incus process.
Figure 3B:
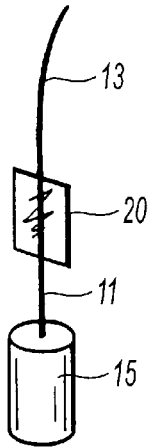
Figure 3C:
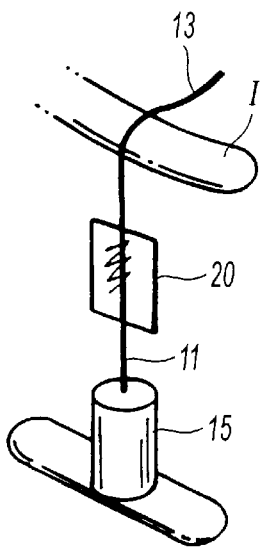
Figure 3D:
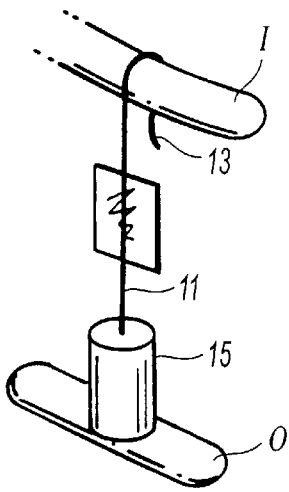

The prosthesis shaft 11 has a lower, or inner, end portion 14 remote from the bight 13, and a fastening means as provided on this end portion for securing the shaft 11 to a second otologic structure, such as the oval window O shown in FIG. 3D. In the embodiment of FIG. 2 the fastening means includes a cylindrical piston 15 of plastic, such as polytetrafluoroethylene (PTFE) molded about the lower end of the shaft 11.

The bight 13 is opened by means of a tool to receive the incus process I and self-closes in response to heat to grip it. In order to accelerate the self-closing action, a heat sink flange 20 is provided on the shaft 11 between the bight 13 and the piston 15. In the illustrated embodiment, the heat sink flange 20 is provided by a flat metal plate which is preferably disposed in a plane transverse to the plane in which the bight 13 is formed, such as orthogonal to the plane of the bight 13. The heat sink flange 20 is secured to the shaft 1 1 as by welding. Thus, the heat sink flange 20 is disposed with its surface area readily exposed to the surgeon for receiving electromagnetic energy, 10 such as may be applied by means of the laser beam customarily used in stapedectomys.

When struck by a laser beam, the heat sink flange 20 conducts heat upwardly along the shaft 11 to the bight 13 causing it to reversely turn on itself into its as manufactured condition for gripping the incus process as illustrated in FIG. 3D. The heat sink flange 20 is also large relative to the shaft 11 to provide a readily visible target for the surgeon to aim the laser beam.

Installation of the prosthesis 10 is straightforward. As best seen in FIG. 2A, the prosthesis 10 is shown in its normal, as manufactured, condition as described with respect to FIG. 2. After removal from the sterile package in the operating theater, the reversely turned bight 13 is straightened as illustrated in FIG. 3B. The prosthesis 10 is installed with its piston 15 engaged with the oval window O, and the bight 13 is loosely engaged with the incus process as illustrated in FIG. 3C. Thereafter, the surgeon applies electromagnetic radiation by a laser to the heat sink flange 20 for heating the shaft 11 and causing the bight 13 to reversely turn on itself to its as manufactured shape and thereby firmly grip the incus process I (FIG. 3D). A temperature of approximately 113° F. (45° C.) is sufficient to cause the bight to reversely turn and engage the incus process I in short order.

Figure 4:
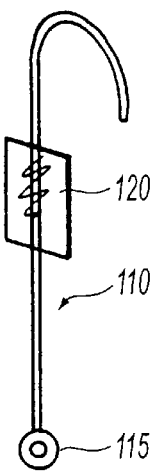
FIG. 4 is an elevational view of another embodiment of an otologic prosthesis according to the present invention.

FIG. 4 illustrates a second embodiment 110 of a prosthesis of the present invention. In the embodiment of FIG. 4, the piston is replaced with a circular loop 115 formed on the bottom of the shaft as in conventional wire prostheses.

Figure 5:
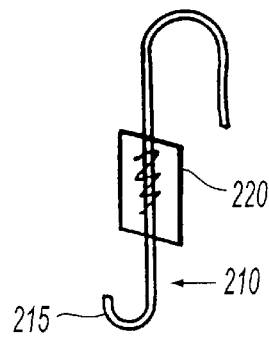
FIG. 5 is an elevational view of a further embodiment of otologic prosthesis according to the present invention.

In the embodiment of FIG. 5, a fastening means is provided by a reversely turned shaft end portion 215, much like the reversely turned upper end bight portion of the shaft illustrated in FIG. 2, but of a smaller radius. The reversely turned lower end portion in the FIG. 5 embodiment is in the same plane as the upper end bight and this embodiment is particularly suited for a malleus to stapes prosthesis.

In both the embodiments of FIG. 4 and FIG. 5, a heat sink flange 120 and 220 is provided for purposes as described above.

Figure 6:
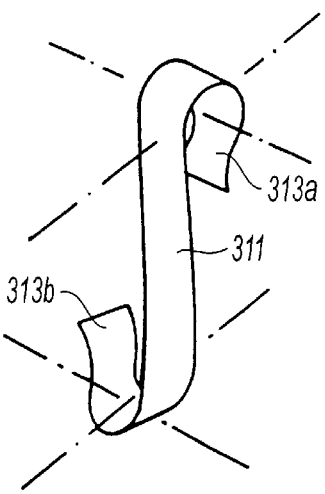
FIG. 6 is an elevational view of yet another embodiment of an otologic prosthesis according to the present invention.

In a further embodiment, illustrated in FIG. 6, the shaft 311 is not of cylindrical wire construction. Rather, it is of a flat ribbon like construction providing upper and lower bights 313a and 313b lying in planes perpendicular to each other. An advantage of this construction is that the ribbon shaft 311 provides a continuous heat sink flange. This embodiment is particularly suited for use in providing an incus to stapes prosthesis.

Figure 7:
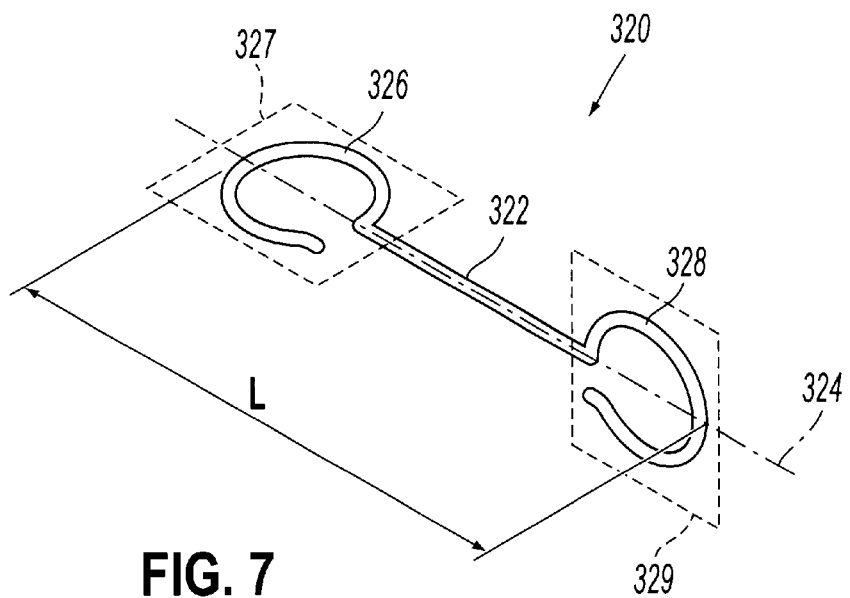
FIGS. 7 and 8 illustrate another embodiment of an otologic prosthesis and its use in a human ear.

Referring to FIG. 7, another example of an otologic prosthesis 320 for connecting, e.g., the malleus to the stapes includes a shaft 322 of nickel-titanium wire substantially disposed on axis 324. A first bight 326 is disposed at one end of shaft 322 and lies substantially in a plane 327. A second bight 328, disposed at the opposing end of shaft 322 and lies substantially in a plane 329, which is positioned about 90 degrees about axis 324 from the first plane 327. Bights 326, 328 have a substantially circular shape with the center disposed on axis 324 and a diameter of about 0.05 mm. Prosthesis 320 has a length L for connecting a malleus and a stapes, which is in the range of about 3 mm to about 5 mm. In this example, a surgeon implanting prosthesis 320 would fasten bights 326, 328 by directing a laser beam on wire 322 as there is no heat sink flange.

Figure 8:
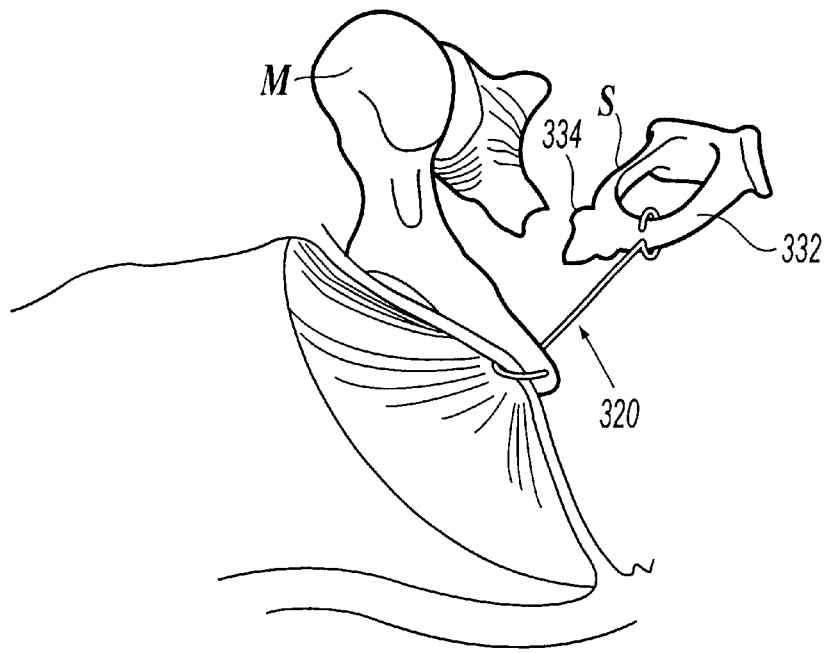

Referring to FIG. 8, prosthesis 320 is shown connecting the malleus to the stapes. In this example, prosthesis 320 is gripping a portion of stapes arch 332. In another example, prosthesis 320 could grip the stapes at capitulum 334, which is the point on the stapes arch to which the incus process normally attaches.

Figure 9:
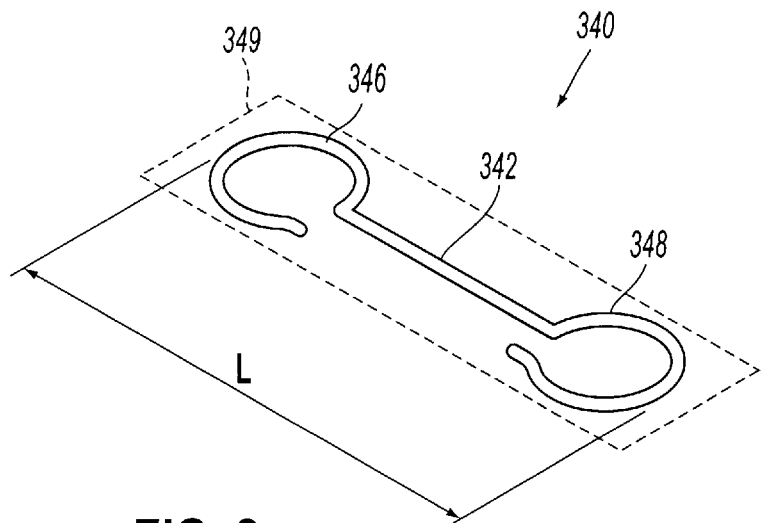
FIGS. 9 and 10 illustrate another embodiment of an otologic prosthesis and its use in a human ear.

Referring to FIG. 9, prosthesis 340 has a shaft 342 with bights 346, 348 formed at each end in a similar size and shape as bights 326, 328 described above. In this example, however, both bights 346, 348 are substantially disposed in a plane 349. Prosthesis 340 has a length L that is suitable for connecting the incus and the stapes arch or capitulum, which is within the range of about 2 mm to about 4 mm.

Figure 10:
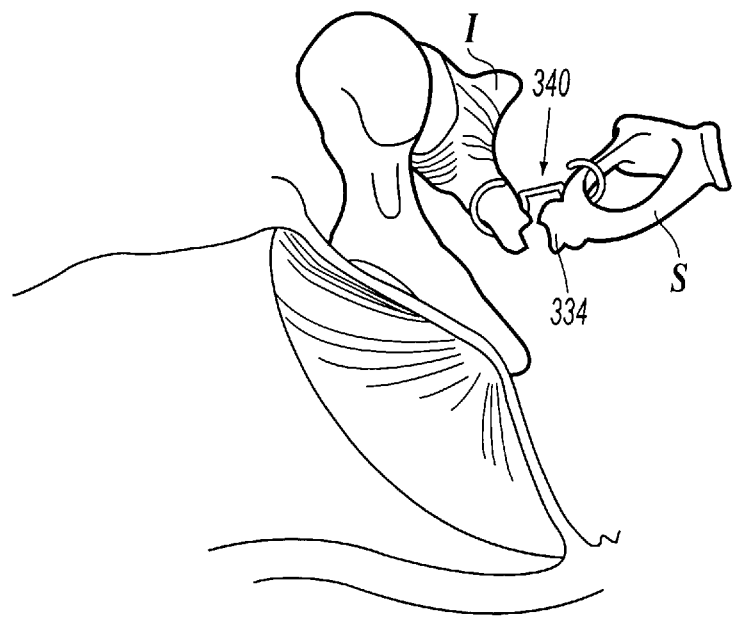

Referring to FIG. 10, prosthesis 340 connects incus I to stapes S. As described above, prosthesis 340 could connect to capitulum 334.

Figure 11:
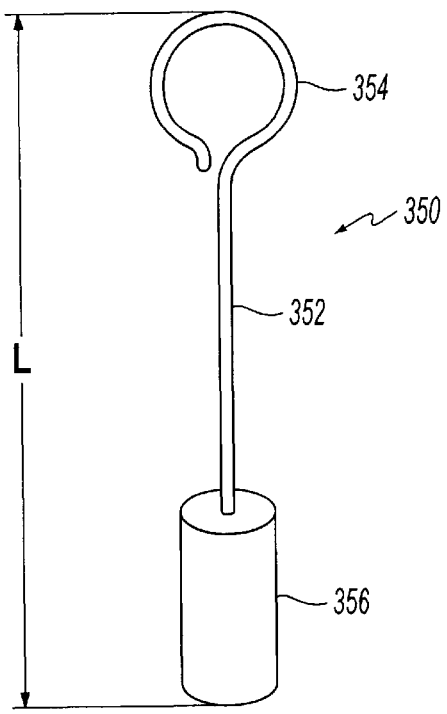
FIGS. 11 and 12 illustrate another embodiment of an otologic prosthesis and its use in a human ear.

Referring to FIG. 11, prosthesis 350 has a shaft 352 of nickel-titanium wire with a bight 354 formed at one end and includes a cylindrical piston 356 of PTFE molded about the opposite end of the shaft 352. Prosthesis 350 has a length L adapted to connect a malleus to a footplate or an oval window, which is in the range of about 7 mm to about 10 mm.

Figure 12:
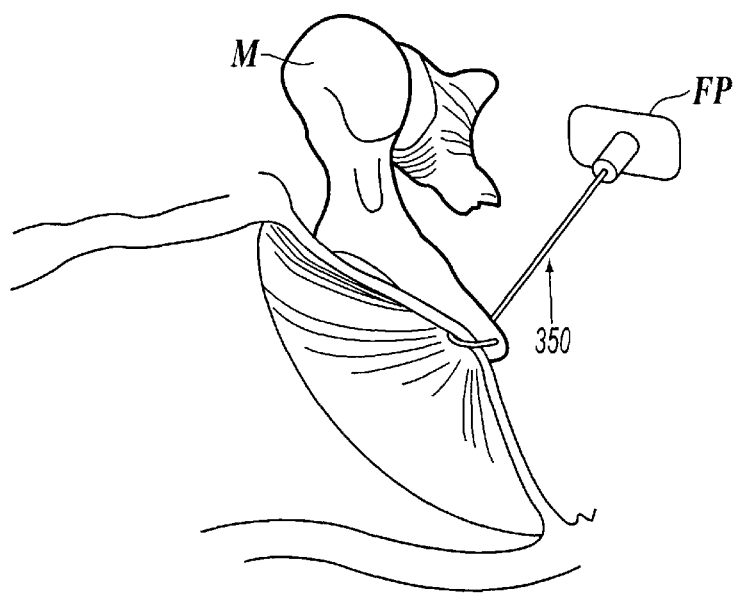

Referring to FIG. 12, prosthesis 350 connects malleus M to stapes footplate FP.

Figure 13:
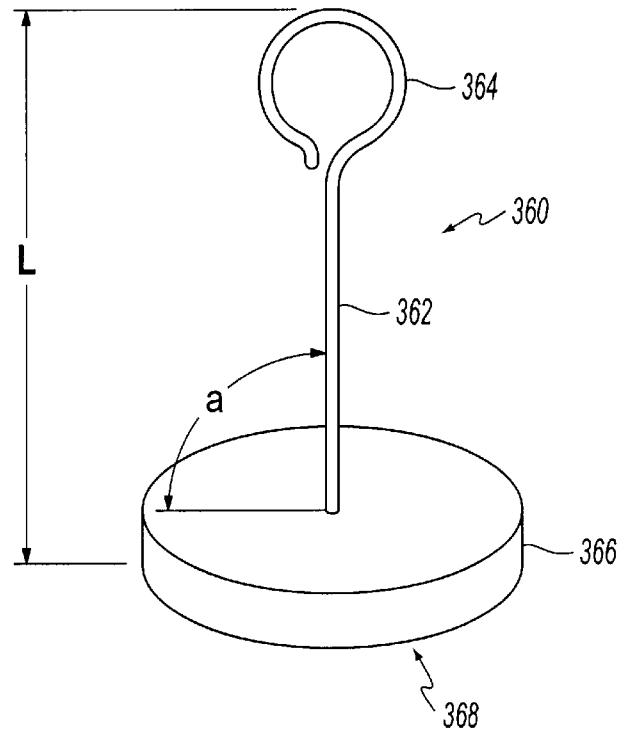
FIGS. 13, 14, and 15 illustrate another embodiment of an otologic prosthesis and two ways it could be used in a human ear.

Referring to FIG. 13, prosthesis 360 has a shaft 362 of nickel-titanium wire with bight 364 formed at one end of shaft 362. On the opposite end of shaft 362, prosthesis 360 includes a cylindrical disk 366 of PTFE molded about shaft 362. Disk 366 has a diameter of about 3 mm and a thickness of about 1 mm. Surface 368 of disk 366 is enlarged with respect to the cross-section of shaft 362, is substantially planar, and is configured to engage an eardrum and conduct sound vibrations from disk 366, through shaft 362, and to an ossicle engaged by bight 364, which could be an incus, stapes arch, or capitulum. Disk 366 is disposed at the end of shaft 362 such that surface 368 is substantially perpendicular to shaft 362 (i.e., angle a is 90 degrees). Alternatively, disk 366 could be disposed such that angle a is within the range of about 90 degrees to about 30 degrees to permit bight 364 to connect to different ossicles. A cyanoacrylate adhesive, such as Dermabond, available from Ethicon Corp. of Cincinnati, Ohio, disposed between an eardrum and surface 368 could engage prosthesis 360 with the eardrum. Prosthesis 360 has a length L permitting connection of an eardrum to an incus, which is within the range of about 2 mm to about 4 mm. In another example, prosthesis 360 has a length L permitting connection of an eardrum to a stapes arch or capitulum, which is within the range of about 4 mm to 6 mm.

Figure 14:
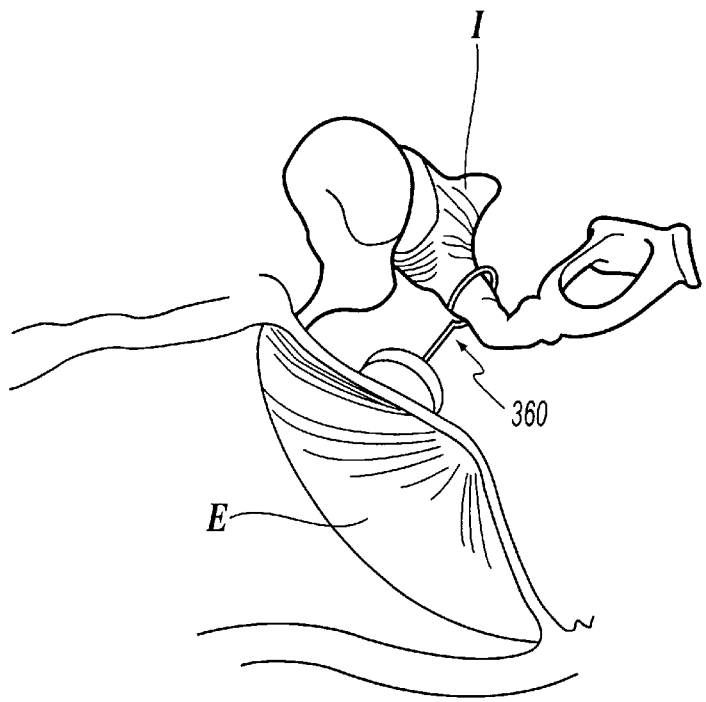

Referring to FIG. 14, an example of prosthesis 360 connecting eardrum E to incus I is shown.

Figure 15:
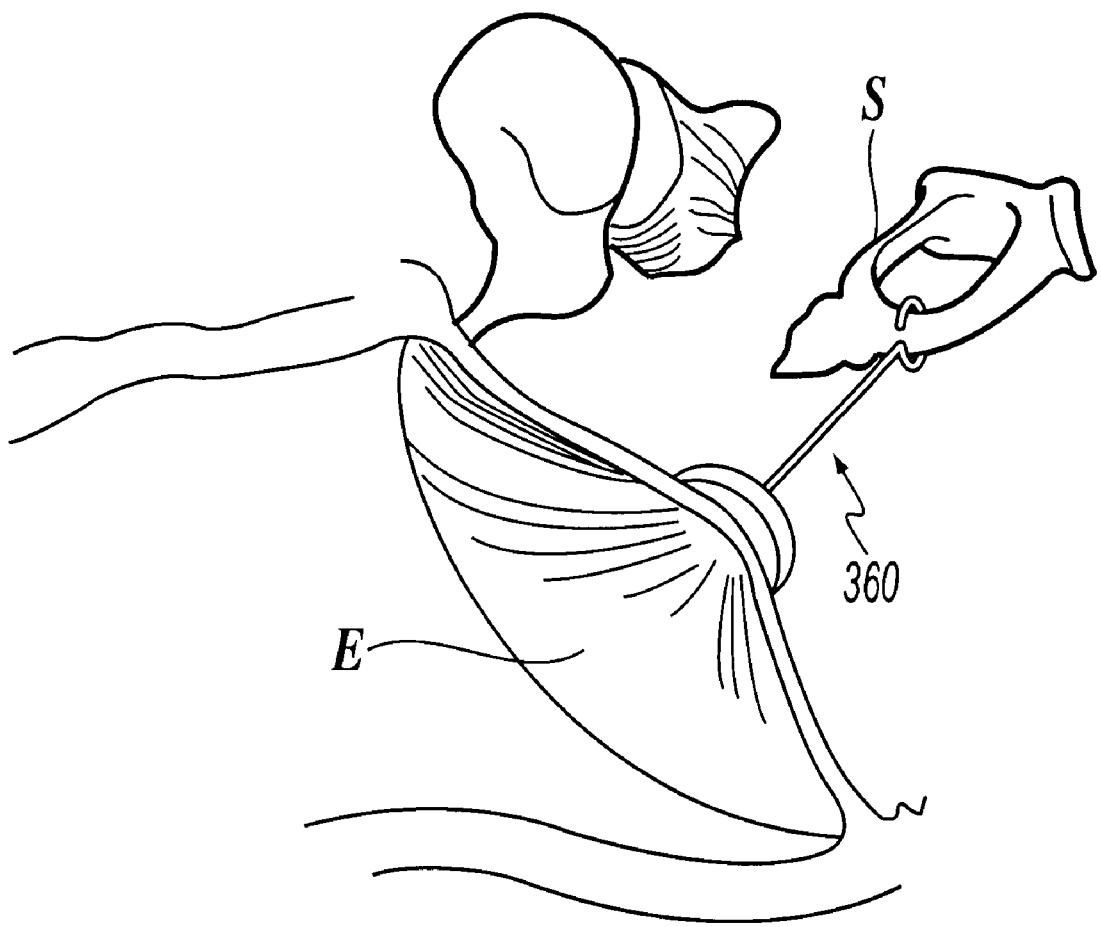

Referring to FIG. 15, an example of prosthesis 360 connecting eardrum E to stapes S is shown.

In view of the foregoing, it should be apparent that the present invention now provides otologic prostheses which overcome many of the limitations of prior art prostheses by eliminating the need for crimping wire about an otologic structure and the concomitant disadvantages associated therewith.

While preferred embodiments of the present invention have been described in detail, various modifications, alterations and changes may be made without departing from the spirit and scope of the present invention as defined in the appended claims.

What is claimed is:

1. Apparatus comprising:
    an elongated member comprising a first end and a second end;
    said first end defining a first bight lying substantially in a first plane, said first end being deformable to open said first bight to receive a first otologic structure and configured to substantially close the first bight in response to an applied signal thereby to capture the first otologic structure; and
    said second end defining a second bight lying substantially in a second plane transverse to the first plane, said second end being deformable to open said second bight to receive a second otologic structure and being configured to substantially close the second bight in response to an applied signal thereby to capture the second otologic structure with the second bight.

2. The apparatus of claim 1 wherein the first otologic structure is a malleus.

3. The apparatus of claim 2 wherein the second otologic structure is a portion of the stapes arch.

4. The apparatus of claim 2 wherein the second otologic structure is a capitulum.

5. The apparatus of claim 1 wherein the first otologic structure is an incus.

6. The apparatus of claim 5 wherein the second otologic structure is a portion of the stapes arch.

7. The apparatus of claim 5 wherein the second otologic structure is a capitulum.

8. The apparatus of claim 1 wherein the member is formed of biocompatible shape-memory alloy.

9. Apparatus comprising:
    an elongated member comprising a first end and a second end;
    said first end defining a first bight lying substantially in a plane, said first end being deformable in response to an applied signal to open said first bight to receive a first otologic structure and being configured to substantially close the first bight in response to an applied signal thereby to capture the first otologic structure; and
    said second end defining a second bight lying substantially in said plane, said second end being deformable in response to an applied signal to open said second bight to receive a second otologic structure and being configured to substantially close the second bight in response to an applied signal thereby to capture the second otologic structure.

10. The apparatus of claim 9 wherein the first otologic structure is an incus.

11. The apparatus of claim 10 wherein the second otologic structure is a portion of the stapes arch.

12. The apparatus of claim 10 wherein the second otologic structure is a capitulum.

13. The apparatus of claim 9 wherein the member is formed of biocompatible shape-memory alloy.

14. Apparatus comprising:
    an elongated member comprising a body, a first end and a second end;
    said first end defining a first bight, said first end being deformable in response to an applied signal to open said first bight to receive a first otologic structure and being configured to substantially close the first bight in response to an applied signal thereby to capture the first otologic structure; and
    said second end of said member comprising an enlarged surface area sized and oriented to lie substantially flat against and be secured to a second otologic structure.

15. The apparatus of claim 14 wherein the enlarged surface is substantially planar.

16. The apparatus of claim 14 wherein the enlarged surface area is oriented at an angle to a longitudinal axis of the body of the member within the range of about 30 degrees to about 90 degrees.

17. The apparatus of claim 14 wherein the second otologic structure is an eardrum.

18. The apparatus of claim 14 further comprising an adhesive for securing the enlarged surface to the second otologic structure.

19. The apparatus of claim 14 wherein the first otologic structure is an incus.

20. The apparatus of claim 14 wherein the first otologic structure is a portion of a stapes arch.

21. The apparatus of claim 14 wherein the first otologic structure is a capitulum.

22. The apparatus of claim 14 wherein the member is formed of biocompatible shape-memory alloy.

23. A method comprising: providing an otologic implant comprising an end defining a bight; deforming the end to open the bight to receive an otologic structure; and applying a signal to the implant to substantially close the bight and capture the otologic structure.

24. The method of claim 23 wherein the implant includes a second end defining a second bight, and further comprising:
    deforming the second end to open the second bight to receive a second otologic structure; and
    applying a signal to the implant to substantially close the second bight and capture the second otologic structure.

25. The method of claim 23 wherein the signal is heat.

26. The method of claim 23 wherein the otologic structure is a malleus.

27. The method of claim 23 wherein the otologic structure is an incus.

28. The method of claim 23 wherein the otologic structure is a stapes.

29. The method of claim 23 wherein the otologic structure is a capitulum.

30. The apparatus of claim 1, wherein said applied signal is heat.

* * * * *

(12) INTER PARTES REEXAMINATION CERTIFICATE (0147th)
United States Patent
Knox et al.

(10) Number: US 6,554,861 C1
(45) Certificate Issued: *Feb. 23, 2010

(54) OTOLOGIC PROSTHESIS

(75) Inventors: Glenn W. Knox, Jacksonville, FL (US); Harlan Reitan, Collierville, TN (US)

(73) Assignee: The Governor and Company of the Bank of Scotland, Bishopsgate Exchange, London (GB)

Reexamination Request:
No. 95/000,262, May 10, 2007

Reexamination Certificate for:
Patent No.: 6,554,861
Issued: Apr. 29, 2003
Appl. No.: 09/798,400
Filed: Mar. 2, 2001

(*) Notice: This patent is subject to a terminal disclaimer.

Related U.S. Application Data

(63) Continuation-in-part of application No. 09/233,394, filed on Jan. 19, 1999, now Pat. No. 6,197,060.

(51) Int. Cl.
*A61F 2/18* (2006.01)
*A61B 19/00* (2006.01)

(52) U.S. Cl. .......................................... 623/10; 600/25
(58) Field of Classification Search ................. 623/10
See application file for complete search history.

(56) References Cited

U.S. PATENT DOCUMENTS

| | | | |
|---|---|---|---|
| 3,722,003 A | 3/1973 | Walchle | |
| 3,838,468 A | 10/1974 | Armstrong | |
| 3,868,956 A | 3/1975 | Alfidi et al. | |
| 4,655,776 A | 4/1987 | Lesinski | |
| 4,740,209 A | 4/1988 | Gersdorff | |
| 5,219,358 A | 6/1993 | Bendel et al. | |
| 5,514,178 A | * 5/1996 | Torchio | 623/23.69 |
| 5,690,671 A | * 11/1997 | McGurk et al. | 606/200 |
| 5,855,577 A | 1/1999 | Murphy-Chutorian et al. | |
| 5,989,242 A | * 11/1999 | Saadat et al. | 606/1 |
| 6,066,083 A | 5/2000 | Slater et al. | |

FOREIGN PATENT DOCUMENTS

| | | |
|---|---|---|
| DE | 4210235 C1 | 11/1993 |
| EP | 0909554 A1 | 4/1999 |
| WO | WO-A 98/24371 | 6/1998 |

OTHER PUBLICATIONS

Evintur, Abraham, *Otologic Medicine and Surgery*, Chapter 46, "Stapes Surgery," pp. 1261–1267.
Schukneehi, Harold F., *Surgery of the Ear and Temporal Bone*, Chapter 20, "Otosclerosis Surgery," pp. 223–239.
Enatsu, Kunitoshi, English Translation of "Utilization of Ni–Ti Shape Memory Alloy for Ossicular Prosthesis and its Biocompatability with the Incus of Cats," *Jibi to Rinsho* [*Otologica Fukuoka*], 32, 256–269 (1986).
Fujihiko Kasano et al., "Utilization of nickel–titanium shape memory alloy for scapes prosthesis," *Auris Narus Larnyx*, vol. 24, pp. 137–142 (1997).
Jurgen Theissing, "HNO–Operationsichre," pp. 352, 382, George Thieme Verlag Stuttgart (1996).
Dietrich Plester et al., "Atlas der Ohrchirugie," pp. 98, 107, 108, 110, Kohlhammer Verlag Stuttgart (1989).
Hans–Georg Boenninghaus, "Hals–Nasen–Ohrenheilkunde," pp. 138, 139, Springer verlag Berlin (1996).
Enatsu, K., Utilixation of Ni–Ti shape memory alloy for ossicular prosthesis and its bicompatibility with the incus of cats, Otologia Fukuoka 32 (1986 256–269 ('Enatsu') (translation provided).
Kasano F., Utilization of nickel–titanium shape memory alloy for stapes prosthesis, Auris Nasus Laryns 24 (1997) 137–142 ('Kasano').

* cited by examiner

*Primary Examiner*—David O. Reip

(57) ABSTRACT

Otologic prosthesis of shape memory metal alloy self-secure about an otologic structure when heat is applied to a preformed bight by means of a laser.

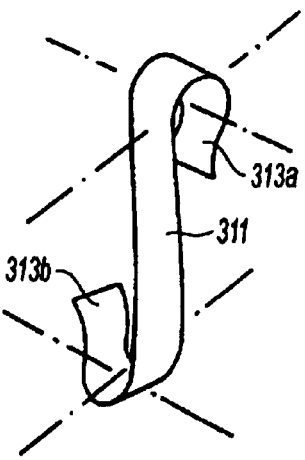

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1–8 and 23–30 are cancelled.
Claims 9–22 were not reexamined.

\* \* \* \* \*